(12) United States Patent
Hayashi

(10) Patent No.: US 11,337,889 B2
(45) Date of Patent: May 24, 2022

(54) ELECTROMAGNETIC-WAVE TREATMENT DEVICE

(71) Applicant: Susa Inc., Okayama (JP)

(72) Inventor: Yukinori Hayashi, Okayama (JP)

(73) Assignee: Susa Inc., Okayama (JP)

( * ) Notice: Subject to any disclaimer, the term of this patent is extended or adjusted under 35 U.S.C. 154(b) by 564 days.

(21) Appl. No.: 16/345,825

(22) PCT Filed: Jul. 21, 2017

(86) PCT No.: PCT/JP2017/026570
§ 371 (c)(1),
(2) Date: Apr. 29, 2019

(87) PCT Pub. No.: WO2018/083845
PCT Pub. Date: May 11, 2018

(65) Prior Publication Data
US 2019/0262228 A1    Aug. 29, 2019

(30) Foreign Application Priority Data
Nov. 1, 2016 (JP) .............................. JP2016-214027

(51) Int. Cl.
*A61H 39/00* (2006.01)
*A61H 39/08* (2006.01)
(Continued)

(52) U.S. Cl.
CPC ............. *A61H 39/00* (2013.01); *A61H 39/08* (2013.01); *A61H 39/086* (2013.01);
(Continued)

(58) Field of Classification Search
None
See application file for complete search history.

(56) References Cited

U.S. PATENT DOCUMENTS 6,004,304 A    12/1999  Suzuki et al.
6,022,368 A *  2/2000   Gavronsky ............ A61H 39/08
                                                      606/189
(Continued)

FOREIGN PATENT DOCUMENTS

JP    H0231767 A     2/1990
JP    H04016679 Y2   4/1992
(Continued)

OTHER PUBLICATIONS

International Search Report for Serial No. PCT/JP2017/026570 dated Sep. 19, 2017.

*Primary Examiner* — Shirley X Jian
(74) *Attorney, Agent, or Firm* — McCormick, Paulding & Huber PLLC

(57) ABSTRACT

The shoulder stiffness, the muscle fatigue, etc., are easily and efficiently improved by the electromagnetic waves without the usage of the power supplies and the large treatment tools. The electromagnetic-wave treatment device 10 has an antenna acupuncture needle 13 and a fixing member 12. The antenna acupuncture needle 13 has a sharp end portion 13*a* having one end portion formed into a needle shape. The fixing member is fixed to the antenna acupuncture needle 13. This antenna acupuncture needle 13 is fixed so that the sharp end portion 13*a* of the antenna acupuncture needle 13 protrudes from the fixing member 12. And, the antenna acupuncture needle 13 functions as an antenna receiving the electromagnetic waves in a space.

4 Claims, 7 Drawing Sheets

(51) Int. Cl.
*A61L 24/00* (2006.01)
*A61N 1/04* (2006.01)

(52) U.S. Cl.
CPC ............ *A61L 24/0005* (2013.01); *A61N 1/04* (2013.01); *A61H 2039/005* (2013.01)

(56) References Cited

U.S. PATENT DOCUMENTS

| | | | | |
|---|---|---|---|---|
| 6,575,992 | B1* | 6/2003 | Takakura | A61H 39/08 606/189 |
| 2012/0035688 | A1* | 2/2012 | Hancock | A61B 18/1815 607/76 |
| 2013/0345782 | A1* | 12/2013 | Kambouris | A61N 1/328 607/116 |
| 2014/0121644 | A1* | 5/2014 | Fischell | A61B 18/00 604/510 |
| 2014/0323837 | A1* | 10/2014 | Hirshberg | A61B 5/15 600/365 |
| 2017/0001003 | A1* | 1/2017 | Pivonka | A61B 5/4836 |

FOREIGN PATENT DOCUMENTS

| | | |
|---|---|---|
| JP | 2982122 B1 | 11/1999 |
| JP | 2000051315 A | 2/2000 |
| JP | 2008113714 A | 5/2008 |

* cited by examiner

ELECTROMAGNETIC-WAVE TREATMENT DEVICE

CROSS-REFERENCE TO RELATED APPLICATION

This application is a National Stage application of International Patent Application No. PCT/JP2017/026570, filed on Jul. 21, 2017, which claims priority to Japanese Patent Application No. 2016-214027, filed on Nov. 1, 2016, each of which is hereby incorporated by reference in its entirety.

TECHNICAL FIELD

The present invention relates to an electromagnetic-wave treatment device, and, more particularly relates to a technique that is effective for treatment promoting blood circulation by using electromagnetic waves.

BACKGROUND

As electronic devices for treatment of shoulder stiffness, for example, alternating-current magnetic treatment devices are known. Such a type of the alternating-current magnetic treatment devices promotes the blood circulation to relax the stiffness by exposing a human body to alternating-current magnetic field generated by using a commercial power supply or others that is a household power supply, in other words, to electromagnetic waves.

As other techniques for promoting the blood circulation to relax the stiffness, acupuncture treatments are popularly treated. Such an acupuncture treatment relaxes the stiffness by using acupuncture stimulation caused by inserting an acupuncture needle into a pressure point or others existing on entire body.

Note that acupuncture needles used for such a type of the acupuncture treatments include, for example, a short acupuncture needle that hardly causes insertion feeling because the short acupuncture needle is extremely shallowly inserted into a skin (see, for example, a Japanese Patent Application Laid-Open Publication No. 2008-113714). This Japanese Patent Application Laid-Open Publication No. 2008-113714 describes that a push-pin-shaped acupuncture needle is prepared so that a needle tip of a needle body is fixed to a disk-shaped base while protruding therefrom and is held by an adhesive bandage to be used.

SUMMARY

However, the above-described alternating-current magnetic field treatment device needs a treatment device that generates the alternating-current magnetic field, and therefore, is highly costed. And, the treatment device needs the commercial power supply as an operational power supply. Therefore, in the treatment, a patient needs to move to a setting place of the treatment device, and therefore, these devices cause a problem of, for example, failing to easily perform the treatments anywhere.

Meanwhile, in the case of the acupuncture treatment using the short acupuncture needle, muscle stiffness in a portion to which the acupuncture short needle is inserted can be relaxed. However, an effect of this case may be limited in comparison with the alternating-current magnetic field treatment device that exposes the human body to the alternating-current magnetic field.

An object of the present invention is to provide a technique capable of easily and efficiently improving the shoulder stiffness, muscle fatigue, etc., by using the electromagnetic waves without using power supplies, large treatment tools, etc.

The above and other objects and novel characteristics of the present invention will be apparent from the description of the present specification and the accompanying drawings.

The summary of the typical aspects of the inventions disclosed in the present application will be briefly described as follows.

That is, a typical electromagnetic-wave treatment device has an acupuncture needle portion having one end formed into a needle shape and a fixing member configured to fix the acupuncture needle portion. The acupuncture needle portion is fixed so that the needle-shaped end of the acupuncture needle portion protrudes from the fixing member, and the acupuncture needle portion functions as an antenna that receives electromagnetic waves in a space.

Particularly, the acupuncture needle portion receives electromagnetic waves in a frequency band used for mobile phone communication.

The effects obtained by the typical aspects of the invention disclosed in the present application will be briefly described below.

The shoulder stiffness, the muscle fatigue, etc., can be easily and efficiently improved at a low cost.

BRIEF DESCRIPTIONS OF THE DRAWINGS

DETAILED DESCRIPTION

In the embodiments described below, the invention will be described in a plurality of sections or embodiments when required as a matter of convenience. However, these sections or embodiments are not irrelevant to each other unless otherwise stated, and the one relates to the entire or a part of the other as a modification example, details, or a supplementary explanation thereof.

Also, in the embodiments described below, when referring to the number of elements (including number of pieces, values, amount, range, and the like), the number of the elements is not limited to a specific number unless otherwise stated or except the case where the number is apparently limited to a specific number in principle. The number larger or smaller than the specified number is also applicable.

Further, in the embodiments described below, it goes without saying that the components (including element steps) are not always indispensable unless otherwise stated or except the case where the components are apparently indispensable in principle.

Similarly, in the embodiments described below, when the shape of the components, positional relation thereof, and the like are mentioned, the substantially approximate and similar shapes and the like are included therein unless otherwise stated or except the case where it is conceivable that they are apparently excluded in principle. The same goes for the numerical value and the range described above.

Also, the same components are denoted by the same reference symbols throughout all the drawings for describing the embodiments, and the repetitive description thereof is omitted. Also, hatching is used even in a plan view so as to make the drawings easy to see.

First Embodiment

<Configuration Example of Electromagnetic-Wave Treatment Device>

The embodiments will be described in detail below.

Figure 1:
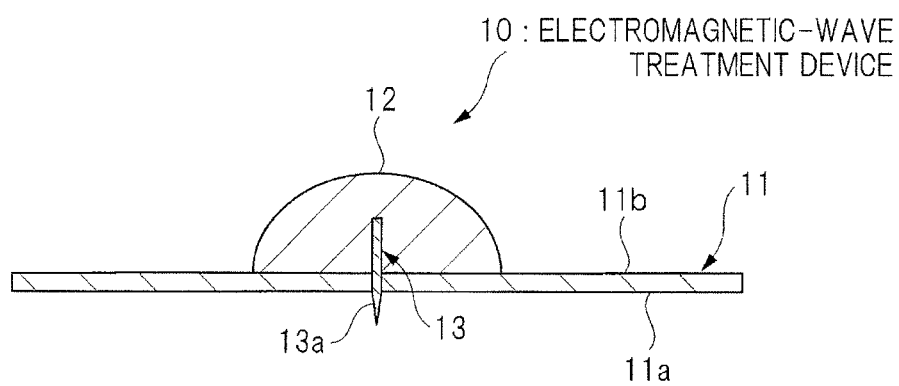
FIG. 1 is a cross-sectional view showing one example of a configuration of an electromagnetic-wave treatment device according to a first embodiment.
Figure 2:
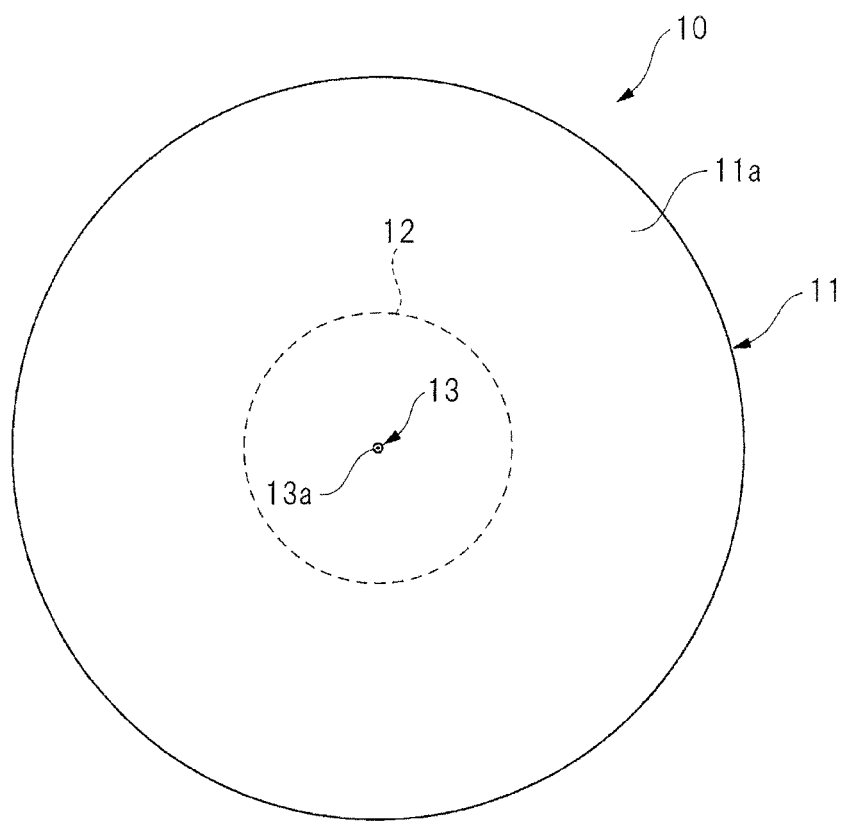
FIG. 2 is a bottom view of the electromagnetic-wave treatment device in FIG. 1.

FIG. 1 is a cross-sectional view showing one example of a configuration of an electromagnetic-wave treatment device 10 according to the present embodiment. FIG. 2 is a bottom view of the electromagnetic-wave treatment device 10 in FIG. 1.

As shown in FIGS. 1 and 2, the electromagnetic-wave treatment device 10 has an adhesive tape 11, a fixing member 12, and an antenna acupuncture needle 13. The adhesive tape 11 has, for example, a circular shape, and one surface of the adhesive tape is an adhesive surface 11a. Note that FIG. 2 shows an example of view of the electromagnetic-wave treatment device 10 in FIG. 1 from the adhesive surface side of the adhesive tape 11.

The fixing member 12 is a base for fixing the antenna acupuncture needle 13. This fixing member 12 has, for example, a semispherical shape, and a diameter of the fixing member is smaller than that of the fixing member 12. In the fixing member 12, a flat surface of the fixing member 12 is adhered onto a surface 11b of the adhesive tape 11. The surface 11b is a surface facing the adhesive surface 11a.

The fixing member 12 is made of a resin that can adhere on metal, that is, a metallic adhesive resin, such as a resin of 4META (4-MEthacryloxyethyl Trimellitate Anhydride). The 4META adhesively fixes the antenna acupuncture needle 13 described later, and adheres the fixing member 12 onto the surface 11b of the adhesive tape 11.

Note that the material of the fixing member 12 for adhesively fixing the antenna acupuncture needle 13 is not limited to the resin such as 4META, and any material may be applicable as long as the material is a material such as a dental metal primer that has no damage to the human body and can adhesively fix the antenna acupuncture needle 13.

The shape of the adhesive tape 11 may be a different shape from the circular shape, and may be, for example, a polygonal shape such as a quadrangular shape. Similarly, the shape of the fixing member 12 is not limited, and may be a polygonal shape such as a disk shape and a quadrangular shape.

The antenna acupuncture needle 13 that is the acupuncture needle portion is made of a rod having a circular cross-sectional surface, that is, made of a round rod, and a needle-shaped and pointed sharp end portion 13a is formed on one end of the antenna acupuncture needle 13. The sharp end portion 13a protrudes from the adhesive surface 11a of the adhesive tape 11 on which the fixing member 12 is adhered, and other portions of the antenna acupuncture needle 13 are adhesively fixed so as to be buried in the fixing member 12.

The antenna acupuncture needle 13 is an acupuncture needle inserted into a skin of a patient, and is made of a material such as stainless steel or others. Specifically, when the adhesive surface 11a of the adhesive tape 11 is pasted on the skin of the patient, the sharp end portion 13a of the antenna acupuncture needle 13 protruding from the adhesive surface 11a is inserted into the skin.

Note that the section of the embodiment has described the example of the pasting of the electromagnetic-wave treatment device 10 on the skin through the adhesive tape 11. However, the flat surface of the fixing member 12 may be pasted on the skin by, for example, coating the flat surface of the fixing member 12 with an adhesive or others.

The antenna acupuncture needle 13 functions as an antenna receiving the electromagnetic waves that fly here and there in the space. As a lot of the electromagnetic waves that fly here and there in the space, for example, electromagnetic waves in a frequency band used for mobile phones are cited.

Therefore, in this embodiment, the antenna is an antenna receiving electromagnetic waves in a 2-GHz frequency band as the frequency band at which the electromagnetic waves can be efficiently received. The 2-GHz frequency band is a frequency band used for LTE (Long Term Evolution) that is one of data communication standards for the mobile phones.

Note that the material of the antenna acupuncture needle 13 is not limited to the above-described stainless steel, and any material may be applicable as long as the material has no damage to the human body and can function as the antenna receiving the electromagnetic waves.

In this embodiment, the 2-GHz frequency band used for the LTE is about from 1920 MHz to 2200 MHz. In the manner, the electromagnetic waves that fly here and there in the space can be efficiently received.

Therefore, an entire length of the antenna acupuncture needle 13, that is, an antenna length is set to a length suitable for receiving the electromagnetic waves in the 2-GHz frequency band used as the frequency bands for the LTE.

When electromagnetic waves in 2.1-GHz frequency band of the 2-GHz frequency band are received, a wave length "λ" in the frequency of 2.1 GHz is about 142.85 mm. The wave length λ can be obtained from an expression 1.

"Wave Length λ"="Speed of Light(300000 km/s)"/ "Frequency [Hz]" (Expression 1)

The antenna length in which the above-described wave length λ of about 142.85 mm can be efficiently received can be obtained from the following expression.

"Antenna Length $L$"=$\lambda/2N$ (Expression 2)

When "N=32" is applied to the expression 2, the entire length of the antenna acupuncture needle 13 is about 2.232 mm. In the manner, the antenna length can be set so as to handle the frequency of 2.1 GHz, and therefore, the electromagnetic waves can be efficiently received.

When the length of the antenna acupuncture needle 13 protruding from the adhesive surface 11a of the adhesive tape 11 is, for example, about 0.3 mm, the length of the antenna acupuncture needle 13 buried in the fixing member 12 is about 1.922 mm.

Note that one example has been shown as the length of the antenna acupuncture needle 13, and the length of the antenna acupuncture needle 13 can be appropriately adjusted on the basis of the expression 2.

If the sharp end portion 13a of the antenna acupuncture needle 13 protruding from a main surface of the fixing member 12 is too long, there is a risk of causing feeling of pain or others in the insertion. If it is too short, there is a risk of failing to exactly insert the acupuncture needle into the skin. Therefore, as the length by which the acupuncture needle is exactly inserted into the skin while the insertion feeling is hardly caused, about 0.3 mm as described above is better for the protruding length of the antenna acupuncture needle 13.

Note that the length of the sharp end portion 13a of the antenna acupuncture needle 13 protruding from the main surface of the fixing member 12 is one example, and is not particularly limited. The material of the antenna acupuncture needle 13 is not particularly limited, either, and any material may be applicable as long as the material is a material such as aluminum having no damage to the human body and favorably functioning as the antenna.

<Treatment Example Using Electromagnetic-Wave Treatment Device>

Subsequently, a mechanism of the electromagnetic-wave treatment device 10 will be described.

Figure 3:
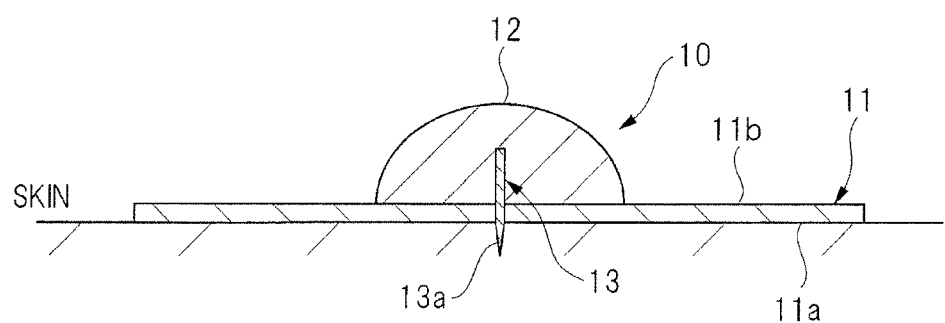
FIG. 3 is an explanatory diagram showing one example caused when the electromagnetic-wave treatment device in FIG. 1 is pasted on a skin of a patient.

FIG. 3 is an explanatory diagram showing one example caused when the electromagnetic-wave treatment device 10 in FIG. 1 is pasted on the skin of the patient.

First, as shown in FIG. 3, when the electromagnetic-wave treatment device 10 is used, the adhesive surface 11a of the adhesive tape 11 of the electromagnetic-wave treatment device 10 is put on the skin of the patient shown in FIG. 3, and the adhesive surface 11a of the adhesive tape 11 is adhered on the skin.

In the manner, the sharp end portion 13a of the acupuncture antenna needle 13 protruding from the adhesive surface 11a of the adhesive tape 11 is inserted into the skin of the patient while the electromagnetic-wave treatment device 10 is adhesively fixed to the skin surface by the adhesive tape 11.

The acupuncture antenna needle 13 receives the electromagnetic waves that fly here and there in the space, more particularly, the electromagnetic waves in the 2-GHz frequency band used for the LTE in the mobile phones, and the acupuncture antenna needle 13 in this embodiment is assumed to be an antenna receiving the electromagnetic waves in about 2.1 GHz.

When the acupuncture antenna needle 13 receives the electromagnetic waves in about 2.1 GHz, the received electromagnetic waves are transformed almost into heat by the wave focusing effect of the acupuncture antenna needle 13 to cause the moxibustion effect because of increase in a temperature of the sharp end portion 13a of the acupuncture antenna needle 13. By this moxibustion effect, the treatments such as the recovery from physical exhaustion, the reduction in the shoulder stiffness, etc., can be performed.

Subsequently, a mechanism of the above-described moxibustion effect will be described.

As an amount for evaluating the thermal effect, for example, SAR (Specific Absorption Rate) is known. This SAR is an energy amount absorbed in tissues per unit mass during unit time when the human body is exposed to the electromagnetic field. In the radiofrequency radiation protection guidelines defined by Ministry of Internal Affairs and Communications in Japan, a local SAR standard value in general residential environment is 2 W/kg.

As an example of the thermal absorption into the human body, the specific absorption rate caused by the moxa (mugwort) moxibustion is considered.

A diameter of a general moxa is about 30 mm, and the moxa has an effect capable of increasing a temperature of an affected portion by 10° C. or higher. Therefore, in assumption that a temperature of muscle tissues in a semispherical portion under a skin surface on which the moxa is put increases by 10° C. or higher, the following relational expression is provided.

Volume with Temperature Increase: $2/3 \times \pi \times (15 \times 10^{-3})$ [m$^3$]

Density of Muscle Tissue: $1.08 \times 10^3$ [kg/m$^3$]

In the above relation expression, a weight of the muscle tissues with the temperature increase is obtained as "volume×density", and therefore, is calculated as $7.63 \times 10^{-3}$ [kg]. The above-described weight of the muscle tissues with the temperature increase is simplified and calculated. It is practically considered that an area of the muscle tissues heated by the moxibustion is larger.

When it is assumed that a specific heat of the muscle tissues is 4.2 [J/g×° C.] as the same as that of water, an amount of heat applied on the muscle tissues heated by the moxibustion is $402 \times 7.63 \times 10$ [J]. When it is assumed that the amount of heat of $402 \times 7.63 \times 10$ [J] is applied to the muscle tissues for, for example, 500 seconds, the specific absorption rate (SAR) is estimated as follows.

[W/kg]=[J/sec/kg]={$(4.2 \times 7.63 \times 10)/500$}/{$7.63 \times 10^{-3}$}=84 [W/kg]

In the manner, when the local SAR is 2 W/kg, the heat effect by the moxibustion, that is, the moxibustion effect causes 84 [W/kg], and therefore, the moxibustion effect per time is about 41 times the effect using the electromagnetic waves to which the human body is daily exposed.

However, when the moxibustion treatment time is set to 15 minutes and the pasting time of the electromagnetic-wave treatment device 10 is set to three days, that is, set to 72 hours, a total amount of heat in this case is 7 in the electromagnetic-wave treatment device 10 with reference to 1 in the moxa, and it can be said that the moxibustion effect mainly causing the thermal effect can be sufficiently expected in the electromagnetic-wave treatment device 10.

The antenna acupuncture needle 13 inserted below the skin is configured to have the antenna function as described above, so that the treatments for the shoulder stiffness, the muscle fatigue, etc., can be performed by only putting the electromagnetic-wave treatment device 10 on the skin of the patient to cause the moxibustion effect due to the increase in the temperature of the sharp end portion 13a of the antenna acupuncture needle 13 when the electromagnetic waves in the space are efficiently received.

The treatments for the shoulder stiffness, the muscle fatigue, etc., can be expected also by the reception of the electromagnetic waves in the space and the exposure of the portion under the skin to the electromagnetic waves in addition to the above-described moxibustion effect.

As to a mechanism for relaxing the shoulder stiffness, the muscle fatigue, etc., by the exposure of the portion under the skin to the electromagnetic waves, for example, the following two points are considered.

First, as to the first point, when the portion under the skin is exposed to the electromagnetic waves, endothelial cells of blood vessels secrete nitric monoxide (NO). It is known that the nitric monoxide becomes a vasodilator mediator, and the vasodilatation is caused by the nitric monoxide to improve the bloodstream.

As to the second point, the electromagnetic waves received by the antenna acupuncture needle 13 are transformed into electric current, and the electric current is energized to the portion under the skin through the antenna acupuncture needle 13, so that muscle tension or others is relaxed.

In the manner, by the reception of the electromagnetic waves in the space and the exposure of the portion under the skin to the electromagnetic waves, the treatments for the shoulder stiffness, the muscle fatigue, etc., can be performed without treatment devices generating the electromagnetic waves.

Therefore, symptoms such as the shoulder stiffness, the muscle fatigue, etc., can be easily improved at a low cost without the usage of the treatment device that needs the power supply such as the commercial power supply.

Since it is only necessary to paste the electromagnetic-wave treatment device 10 on the skin, time for procedure needed in the usage of the treatment device or others is unnecessary, and limitation due to the time for the procedure can be reduced.

In this specification, in order to efficiently receive the electromagnetic waves, note that the electromagnetic waves in the frequency band used for the mobile phones are received as a lot of the electromagnetic waves that fly here and there in the space. However, the received electromagnetic waves may be electromagnetic waves such as that of wireless LAN (Local Area Network) other than the electromagnetic waves in the frequency band used for the mobile phones, and are not limited to the electromagnetic waves. In this case, the antenna acupuncture needle 13 of the electromagnetic-wave treatment device 10 is set to have the length suitable for the reception of the electromagnetic waves in the frequency band to be received.

As described above, the antenna length of the antenna acupuncture needle 13 is set to the length in consideration of the frequency of the electromagnetic waves to be received, so that the electromagnetic waves to be collected can be efficiently limited and collected. And, the electromagnetic-wave treatment devices 10 having different lengths of the antenna acupuncture needles 13 from one another can be pasted on the skin. In the manner, the treatments in consideration of the treatment effect caused by the difference among the frequencies in which the electromagnetic waves are collected can be performed.

When the frequency band used for the mobile phones migrates from 2-GHz frequency band to a different frequency band, electromagnetic waves in the migrated frequency band largely occupy the space.

In this case, by reception of the electromagnetic waves in the migrated frequency band, the electromagnetic waves can be more efficiently received. Also under such circumstances, the antenna acupuncture needle 13 of the electromagnetic-wave treatment device 10 is set to have the length suitable for the reception of the electromagnetic waves in the migrated frequency band.

Note that the section of the present embodiment has described the example in which the antenna acupuncture needle 13 of the electromagnetic-wave treatment device 10 is the whip antenna. However, the shape of the antenna acupuncture needle 13 is not limited to this shape, and may be any shape as long as the antenna acupuncture needle can efficiently receive the electromagnetic waves.

Second Embodiment

<Outline>

A section of the present second embodiment will describe another example of the antenna acupuncture needle 13.

The antenna length of the antenna acupuncture needle 13 included in the electromagnetic-wave treatment device 10 shown in FIG. 1 of the above-described first embodiment is ideally $\lambda/4$. Meanwhile, it is necessary to downsize the electromagnetic-wave treatment device 10 in order to reduce uncomfortable feeling or others in putting it. Therefore, it is also necessary to reduce the antenna length to not $\lambda/4$ but 2N ("N" is an integer number) that is shorter. However, the shorter the antenna length is, the higher a possibility of losing an essential function as the antenna, that is, a function of collecting the electromagnetic waves is.

Accordingly, the section of the present second embodiment will describe the electromagnetic-wave treatment device 10 capable of efficiently collecting the electromagnetic waves without increase in a size of the electromagnetic-wave treatment device 10.

<Configuration Example of Electromagnetic-Wave Treatment Device>

Figure 4:
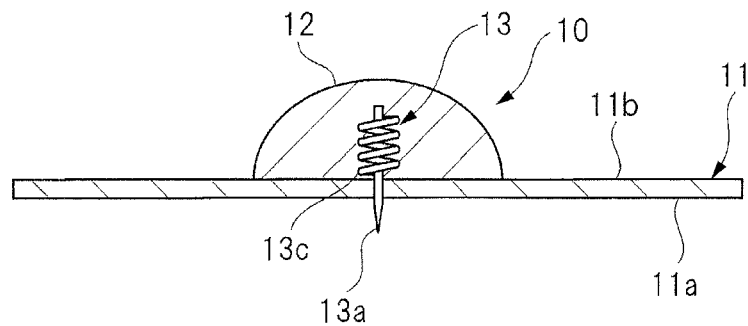
FIG. 4 is a cross-sectional view showing one example of a configuration of an electromagnetic-wave treatment device according to a second embodiment.
Figure 5:
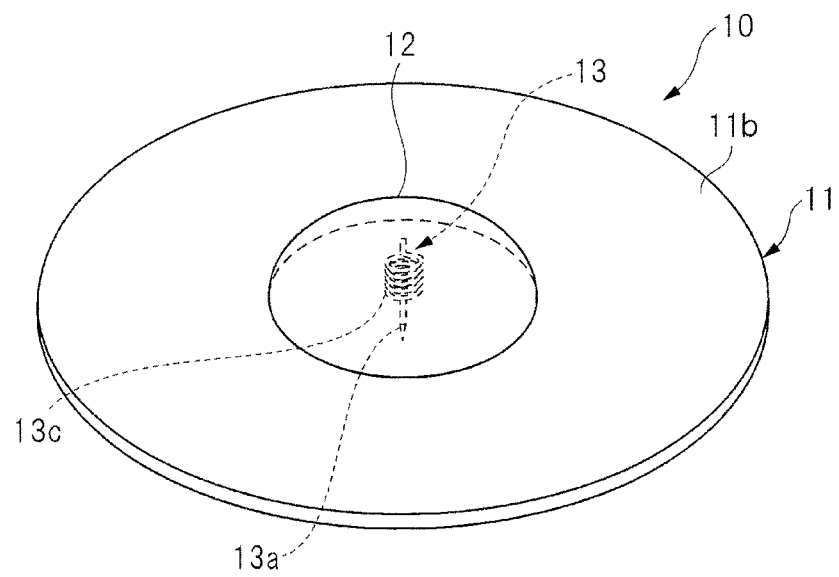
FIG. 5 is an explanatory diagram showing one example of an outline in FIG. 4.

FIG. 4 is a cross-sectional view showing one example of a configuration of the electromagnetic-wave treatment device according to the present second embodiment. FIG. 5 is an explanatory diagram showing one example of an outline in FIG. 4.

A different point of the electromagnetic-wave treatment device 10 shown in FIGS. 4 and 5 from the electromagnetic-wave treatment device 10 in FIG. 1 is the shape of the antenna acupuncture needle 13. As described above, in FIG. 1, the antenna acupuncture needle 13 is the whip antenna. However, the electromagnetic-wave treatment device 10 shown in FIG. 4 is configured so that an extension coil, that is, a coil portion 13c being a loading coil is formed in the antenna acupuncture needle 13.

FIG. 4 shows an example of so-called center load in which the coil portion 13c is formed almost in the middle of the antenna acupuncture needle 13. However, a position of the coil portion 13c is not particularly limited except for the sharp end portion 13a, and the coil portion 13c may be formed at any position causing so-called top load antenna or others at which, for example, it is formed in vicinity of an end portion opposite to the sharp end portion 13a.

In the manner, a part of the antenna acupuncture needle 13 is formed to have a coil shape, so that an electrical length of the antenna can be extended. As a result, the antenna can more efficiently receive the electromagnetic waves without the increase in the physical antenna length than the antenna acupuncture needle 13 in FIG. 1. Other configurations are the same as those of FIGS. 1 and 2, and therefore, the description thereof will be omitted.

As described above, the electromagnetic-wave treatment device 10 can more efficiently receive the electromagnetic waves without being increased in the size. As a result, the moxibustion effect can be more enhanced, and therefore, the symptoms such as the shoulder stiffness, the muscle fatigue, etc., can be easily reduced at a low cost.

Third Embodiment

<Outline>

The shape of the antenna acupuncture needle is not limited to the shapes of the antenna acupuncture needles described in the first and second embodiments, and any shape is applicable as long as the electromagnetic waves can be efficiently received. A section of the present third embodiment will describe another shape example of the antenna acupuncture needle.

<Configuration Example of Electromagnetic-Wave Treatment Device>

Figure 6:
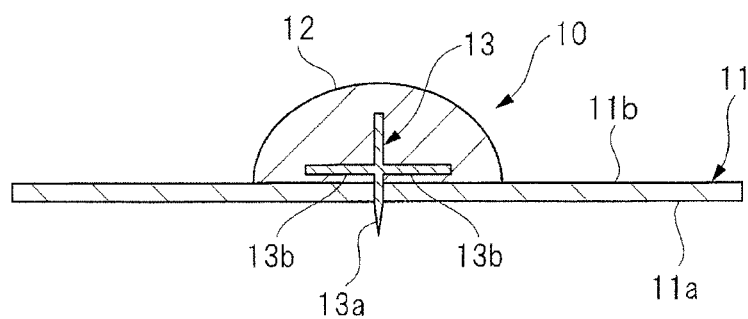
FIG. 6 is a cross-sectional view showing another example of a configuration of an electromagnetic-wave treatment device according to a third embodiment.
Figure 7:
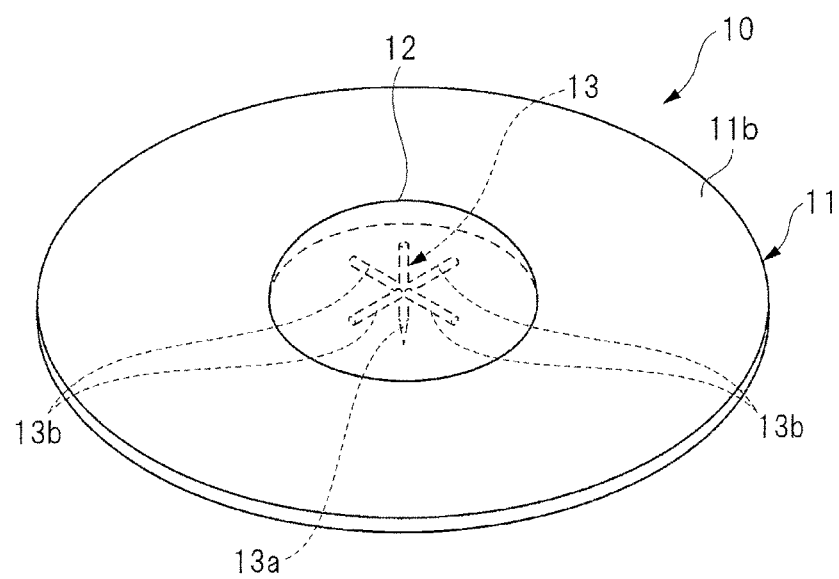
FIG. 7 is an explanatory diagram showing one example of an outline in FIG. 6.

FIG. 6 is a cross-sectional view showing another example of a configuration of the electromagnetic-wave treatment device according to the present third embodiment. FIG. 7 is an explanatory diagram showing one example of an outline in FIG. 6.

In the electromagnetic-wave treatment device 10 in FIG. 1, the antenna acupuncture needle 13 is the whip antenna. However, the electromagnetic-wave treatment device 10 in FIGS. 6 and 7 is configured so that four radials 13b are newly provided to the antenna acupuncture needle 13. Other configurations are the same as those of FIGS. 1 and 2, and therefore, the description thereof will be omitted.

Each of the radials 13b is an element functioning as a simulated earth (ground) terminal, and is attached to the antenna acupuncture needle 13 functioning as a radiation element. Each of these four radials 13b is provided so as to extend from an outer peripheral surface of the antenna acupuncture needle 13 in a radial direction of the antenna acupuncture needle 13, and the adjacent radials 13b are attached at a right angle from each other. That is, this antenna has the same shape as that of a general ground plane antenna.

In the manner, the electromagnetic-wave treatment device 10 can efficiently receive the electromagnetic waves while the increase in the size of the electromagnetic-wave treatment device 10 is suppressed.

<Another Configuration Example of Electromagnetic-Wave Treatment Device>

Figure 8:
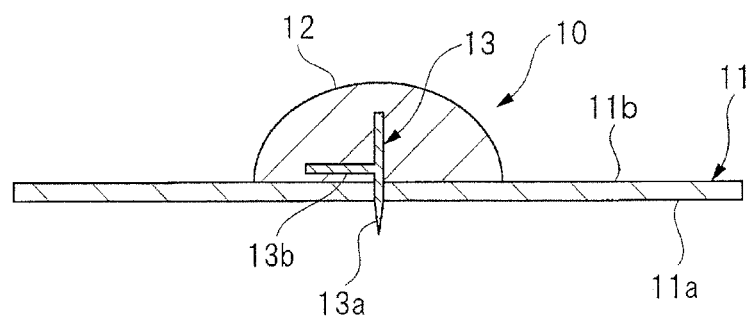
FIG. 8 is a cross-sectional view showing another example of a configuration of the electromagnetic-wave treatment device in FIG. 6.
Figure 9:
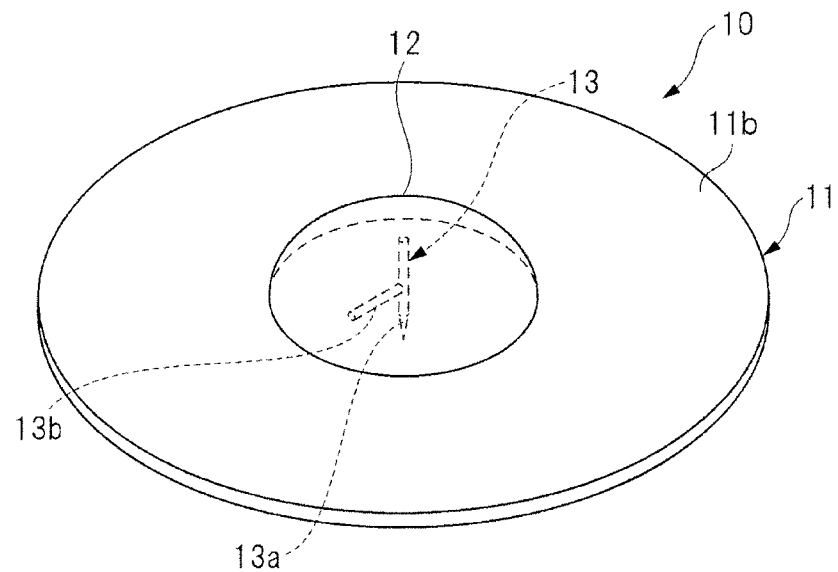
FIG. 9 is an explanatory diagram showing one example of an outline in FIG. 8.

FIG. 8 is a cross-sectional view showing another example of a configuration of the electromagnetic-wave treatment device in FIG. 6. FIG. 9 is an explanatory diagram showing one example of an outline in FIG. 8.

The electromagnetic-wave treatment device 10 in FIGS. 8 and 9 is configured so that one radial 13b is provided to the antenna acupuncture needle 13. The radial 13b is provided so as to extend from an outer peripheral surface of the antenna acupuncture needle 13 in a radial direction of the antenna acupuncture needle 13, and has so-called L-type ground plane antenna shape. Also in the manner, the electromagnetic-wave treatment device 10 can efficiently receive the electromagnetic waves while the increase in the size of the electromagnetic-wave treatment device 10 is suppressed.

Figure 10:
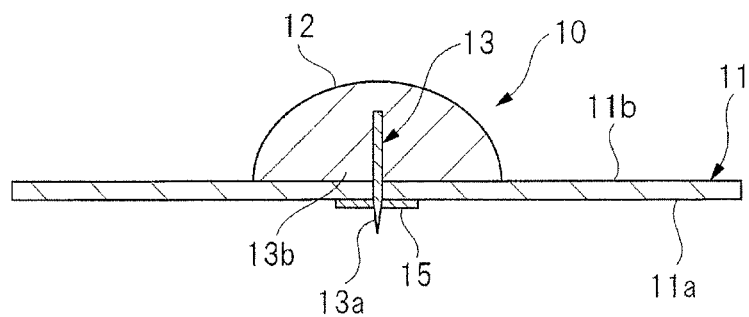
FIG. 10 is a cross-sectional view showing still another example of the configuration of the electromagnetic-wave treatment device in FIG. 6.
Figure 11:
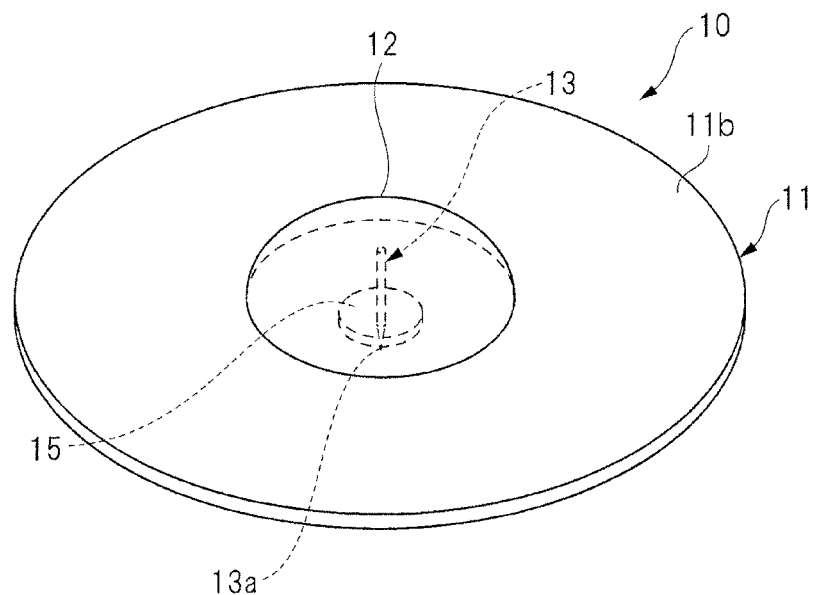
FIG. 11 is an explanatory diagram showing one example of an outline in FIG. 10.

FIG. 10 is a cross-sectional view showing still another example of the configuration of the electromagnetic-wave treatment device in FIG. 6. FIG. 11 is an explanatory diagram showing one example of an outline in FIG. 10.

The electromagnetic-wave treatment device 10 in FIGS. 6 to 9 is configured so that four or one radial 13b is provided to the antenna acupuncture needle 13. However, the electromagnetic-wave treatment device 10 in FIGS. 10 and 11 is configured so that a disk-shaped radial 15 is provided to the adhesive surface 11a of the adhesive tape 11. This radial 15 is made of the same material as, for example, that of the antenna acupuncture needle 13. However, the material of the radial 15 is not limited to this material, and any material is applicable as long as being a conductor.

The sharp end portion 13a of the antenna acupuncture needle 13 is formed so as to penetrate the adhesive surface 11a of the adhesive tape 11 and protrude from almost center of the disk-shaped radial 15. As to a radius of the disk-shaped radial 15, ¼ of the antenna length of the antenna acupuncture needle 13 is the most optimal size.

When the adhesive surface 11a of the adhesive tape 11 is pasted on the skin of the patient, the radial 15 is closely adhered onto the skin of the patient to function as the simulated earth terminal. The sharp end portion 13a of the antenna acupuncture needle 13 protruding from the radial 15 is inserted into the skin.

Also in the manner, the electromagnetic-wave treatment device 10 can efficiently receive the electromagnetic waves while the increase in the size of the electromagnetic-wave treatment device 10 is suppressed.

Figure 12:
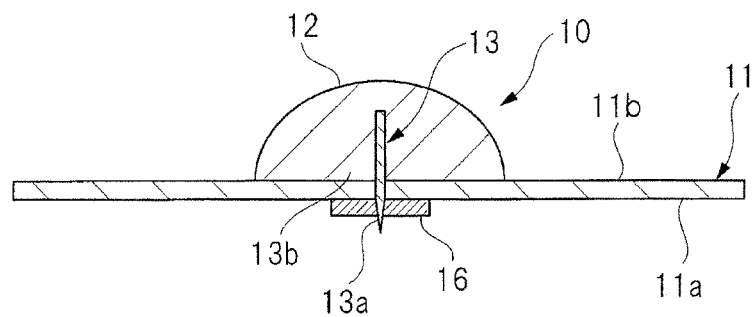
FIG. 12 is a cross-sectional view showing another example of the configuration of the electromagnetic-wave treatment device in FIG. 10.
Figure 13:
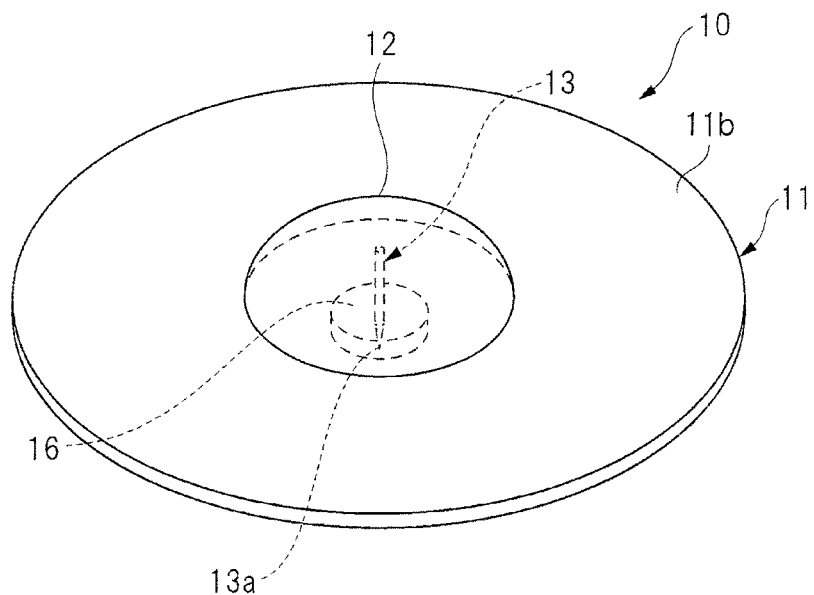
FIG. 13 is an explanatory diagram showing one example of an outline in FIG. 12.

FIG. 12 is a cross-sectional view showing another example of the configuration of the electromagnetic-wave treatment device in FIG. 10. FIG. 13 is an explanatory diagram showing one example of an outline in FIG. 12.

The electromagnetic-wave treatment device 10 in FIGS. 10 and 11 is configured so that the disk-shaped radial 15 is provided to the adhesive surface 11a of the adhesive tape 11. However, the electromagnetic-wave treatment device 10 in FIGS. 12 and 13 is configured so that a disk-shaped resin 16 is provided instead of the radial 15. This radial 15 is made of the same material as, for example, that of the antenna acupuncture needle 13. However, the material of the radial 15 is not limited to this material, and any material is applicable as long as being a conductor.

As shown in FIG. 12, the sharp end portion 13a of the antenna acupuncture needle 13 is formed so as to penetrate the adhesive surface 11a of the adhesive tape 11 and protrude from almost center of the disk-shaped resin 16. When the adhesive surface 11a of the adhesive tape 11 is pasted on the skin of the patient, the resin 16 is closely adhered onto the skin of the patient, so that the skin of the patient becomes the simulated earth terminal, and the resin 16 can be functioned as the radial.

Note that the present invention is not limited to the foregoing embodiments, and include various modifications. For example, the above-described embodiments have been explained in detail for easily understanding the present invention, and are not always limited to the one including all structures explained above.

Also, a part of the structure of one embodiment can be replaced with the structure of another embodiment, and besides, the structure of another embodiment can be added to the structure of one embodiment. Further, another structure can be added to/eliminated from/replaced with a part of the structure of each embodiment.

EXPLANATION OF REFERENCE CHARACTERS 10 electromagnetic-wave treatment device, 11 adhesive tape, 11a adhesive surface, 11b surface, 12 fixing member, 13 antenna acupuncture needle, 13a sharp end portion, 13b radial, 13c coil portion, 15 radial, 16 resin While the present disclosure has been illustrated and described with respect to a particular embodiment thereof, it should be appreciated by those of ordinary skill in the art that various modifications to this disclosure may be made without departing from the spirit and scope of the present disclosure.

What is claimed is:

1. An electromagnetic-wave treatment device comprising:
   an acupuncture needle portion having one end portion formed into a needle shape;
   a fixing member configured to fix the acupuncture needle portion; and
   an adhesive tape configured to adhere the fixing member to a skin,
   wherein the acupuncture needle portion is fixed so that the needle-shaped one end portion of the acupuncture needle portion protrudes from the fixing member,
   the fixing member is formed on a surface facing opposite to an adhesive surface of the adhesive tape,
   the one end portion formed into a needle shape of the acupuncture needle portion protrudes from the adhesive surface of the adhesive tape,
   the acupuncture needle portion functions as an antenna configured for receiving electromagnetic waves in a space,
   the antenna has an antenna length suitable for receiving electromagnetic waves in a frequency band emitted from a mobile phone, and
   blood circulation is improved by absorbing the electromagnetic waves gathered by the antenna into the skin.

2. The electromagnetic-wave treatment device according to claim 1, further comprising
   a circular resin or radial configured to adhere the fixing member to a skin,
   the acupuncture needle portion is fixed so that the one end portion of the acupuncture needle portion protrudes from the center portion of the resin or radial, and
   the resin or radial is adhered to the adhesive surface of the adhesive tape so that the skin functions as a simulated earth terminal when the adhesive surface is adhered to the skin.

3. The electromagnetic-wave treatment device according to claim 1,
   wherein the acupuncture needle portion forms a ground plane antenna having at least one auxiliary element provided so as to extend from an outer peripheral surface of the acupuncture needle in a radial direction of the acupuncture needle.

4. The electromagnetic-wave treatment device according to claim 1,
   wherein a loading coil which extends the electrical length of the antenna is formed in the acupuncture needle portion, and
   the loading coil is formed in the fixing member.

* * * * *